(12) United States Patent
Moon

(10) Patent No.: US 12,285,276 B2
(45) Date of Patent: *Apr. 29, 2025

(54) METHOD FOR PROVIDING ALERT OF POTENTIAL THYROID ABNORMALITY

(71) Applicant: THYROSCOPE INC., Ulsan (KR)

(72) Inventor: Jae Hoon Moon, Seoul (KR)

(73) Assignee: THYROSCOPE INC., Ulsan (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/414,154

(22) Filed: Jan. 16, 2024

(65) Prior Publication Data

US 2024/0148339 A1    May 9, 2024

Related U.S. Application Data

(63) Continuation of application No. 18/091,751, filed on Dec. 30, 2022, now Pat. No. 11,903,743, which is a
(Continued)

(30) Foreign Application Priority Data

Sep. 18, 2017  (KR) .................. 10-2017-0119326

(51) Int. Cl.
*A61B 5/00* (2006.01)
*A61B 5/0205* (2006.01)
(Continued)

(52) U.S. Cl.
CPC ............ *A61B 5/7275* (2013.01); *A61B 5/002* (2013.01); *A61B 5/0205* (2013.01);
(Continued)

(58) Field of Classification Search
CPC ... A61B 5/7275; A61B 5/0205; A61B 5/4227; A61B 5/1118; A61B 5/02438
See application file for complete search history.

(56) References Cited

U.S. PATENT DOCUMENTS 11,571,170 B2 *  2/2023  Moon .................... A61B 5/681
11,937,936 B2 *  3/2024  Moon .................. A61B 5/4848
(Continued)

FOREIGN PATENT DOCUMENTS

CN       105326493 A    2/2016
CN       105708440 A    6/2016
(Continued)

OTHER PUBLICATIONS

International Search Report issued Jun. 18, 2018, corresponding to International Application No. PCT/KR2017/011892.
(Continued)

*Primary Examiner* — Catherine M Voorhees
*Assistant Examiner* — James Moss
(74) *Attorney, Agent, or Firm* — K&L Gates LLP

(57)    ABSTRACT

Provided are a system and a computer program for managing and predicting thyrotoxicosis using a wearable device. The system for predicting thyrotoxicosis is a system for predicting thyrotoxicosis using a resting heart rate, the system including a wearable device for measuring the heart rate of a patient at regular intervals, and a bio-signal computing device for receiving heart rate information from the wearable device, the bio-signal computing device outputting a warning alarm when a resting heart rate is greater than a reference heart rate when the patient is in a normal state.

9 Claims, 8 Drawing Sheets

Related U.S. Application Data continuation of application No. 17/316,040, filed on May 10, 2021, now Pat. No. 11,571,170, which is a continuation of application No. 16/647,963, filed as application No. PCT/KR2017/011892 on Oct. 26, 2017, now abandoned.

(51) Int. Cl.
*A61B 5/024* (2006.01)
*A61B 5/11* (2006.01)

(52) U.S. Cl.
CPC ............ *A61B 5/4227* (2013.01); *A61B 5/681* (2013.01); *A61B 5/721* (2013.01); *A61B 5/02438* (2013.01); *A61B 5/1118* (2013.01)

(56) References Cited

U.S. PATENT DOCUMENTS

| | | | |
|---|---|---|---|
| 2004/0015058 A1* | 1/2004 | Besson | H03F 3/45103 600/27 |
| 2011/0112418 A1* | 5/2011 | Feild | A61B 5/0006 600/509 |
| 2014/0275852 A1 | 9/2014 | Hong et al. | |
| 2014/0276119 A1 | 9/2014 | Venkatraman et al. | |
| 2014/0278125 A1 | 9/2014 | Balakrishnan et al. | |
| 2015/0057512 A1 | 2/2015 | Kapoor | |
| 2015/0094545 A1 | 4/2015 | Russell et al. | |
| 2015/0351690 A1* | 12/2015 | Toth | A61B 5/14542 600/391 |
| 2016/0188817 A1 | 6/2016 | TekWani | |
| 2017/0095159 A1 | 4/2017 | Bonomi et al. | |
| 2018/0035899 A1 | 2/2018 | Gunderson | |
| 2018/0192935 A1 | 7/2018 | Jang et al. | |
| 2018/0256094 A1 | 9/2018 | Russell et al. | |

FOREIGN PATENT DOCUMENTS

| | | |
|---|---|---|
| CN | 106037749 A | 10/2016 |
| CN | 106419848 A | 2/2017 |
| JP | H11290282 A | 10/1999 |
| JP | 2011147509 A | 8/2011 |
| JP | 2015-131049 A | 7/2015 |
| JP | 2016-146622 A1 | 8/2016 |
| JP | 2017-113191 A | 6/2017 |
| KR | 10-2015-0142310 A | 12/2015 |
| KR | 10-2017-0002035 A | 1/2017 |
| KR | 10-2017-0017648 A | 2/2017 |
| KR | 20170017648 A | 2/2017 |
| WO | 2016080911 A1 | 5/2016 |

OTHER PUBLICATIONS

Supportive Materials for Exception to Loss of Novelty] Jae Hoon Moon et al., 'Clinical application of continuous monitoring data for the pulse rate, exercise, and calorie intake by commercially available wearable device in the patients with thyrotoxicosis' From "The 5th Seoul International Congress of Endocrinology and Metabolism": Walkerhill Seoul Hotel, Seoul, Korea, Apr. 27-30, 2017.

Office Action of Japanese Patent Application No. 2020-537119, May 25, 2021.

Kitamura H et al. "Cardiac and plasma catecholamine response to dynamic exercise in hyperthyroidism", Journal of Cardiology, Jan. 1, 1992, 22(1):219-225.

Written Opinion of Internation Application No. PCT/KR2017/011892_2018-06-18.

Extended European Search Report from European Patent Application No. 17924788.7, dated Sep. 10, 2021.

Japanese Office Action from Japanese Patent Application No. 2020-537119, dated Dec. 7, 2021.

Al-Musawy et al., Pulse Rate can be taken as a marker for serum levels of T3 and T4 in thyrotoxic patients, Iraqi J. Comm. Med. Jan. 20, 2007, https://www.iasj.net/iasj/download/5635f048ffce9fbc, viewed on Jul. 15, 21.

Irwin Klein et al., Thyroid Disease and the Heart, Circulation. 2007; 116:1725-1735, https://doi.org/10.1161/CIRCULATIONAHA.106.678326, https://www.ahajournals.org/doi/10.1161/CIRCULATIONAHA.106.678326, viewed on Jul. 13, 2021.

Gammage et al. Association Between Serum Free Thyroxine Concentration and Atrial Fibrillation. Arch Intern Med. 2007;167(9):928-934. doi:10.1001/archinte.167.9.928, https://jamanetwork.com/journals/jamainternalmedicine/fullarticle/412398, viewed on Jul. 13, 2021.

Iqbal et al., Endocrinology—The thyroid and the heart, Apr. 15, 2010, https://www.gponline.com/endocrinology-thyroid-heart/ cardiovascular-system/cardiovascular-system/article/995935, viewed on /14/21.

Faizel Osman et al., Cardiovascular Manifestations of Hyperthyroidism Before and After Antithyroid Therapy: A Matched Case-Control Study, Journal of the American College of Cardiology, vol. 49, Issue 1, 2007, pp. 71-81, https:// www.sciencedirect.com/science/article/pii/S073510970602465X.

Caroline Kee, This Woman's Apple Watch Helped Detect Her Severe Thyroid Problem, Apr. 12, 2018, https:// www.buzzfeednews.com/article/carolinekee/womans-apple-watch-detects-rapid-heart-rate-hyperthyroidism, viewed on Jul. 15, 2021.

* cited by examiner

● Baseline Characteristics of Study Subjects

| (N = 21) | Visit 1 Mean ± SD | Visit 2 Mean ± SD | Visit 3 Mean ± SD |
|---|---|---|---|
| Age, years | 36.7 ± 10.3 | | |
| Height, cm | 165.6 ± 7.6 | | |
| Male (%) | 28.6 | | |
| Weight, kg | 58.0 ± 9.3 | 58.4 ± 8.9 | 58.4 ± 9.8 |
| BMI, kg/m$^2$ | 21.08 ± 2.50 | 21.15 ± 2.48 | 19.88 ± 5.88 |
| SBP, mmHg | 129.5 ± 14.1 | 128.8 ± 14.8 | 131.9 ± 14.6 |
| DBP, mmHg | 78.2 ± 10.6 | 78.8 ± 9.9 | 80.5 ± 8.9 |
| HR, bpm | 105.3 ± 16.3 | 97.1 ± 16.9 | 95.7 ± 16.1 |
| HSS | 14.0 ± 5.3 | 8.3 ± 4.9 | 7.0 ± 5.6 |
| free T4, ng/dl | 3.16 ± 1.16 | 1.93 ± 0.63 | 1.48 ± 0.54 |
| TSH, μIU/ml | 0.08 ± 0.36 | 0.64 ± 2.86 | 0.43 ± 1.17 |
| TSH receptor Ab, IU/l | 18.66 ± 21.81 | 16.89 ± 18.15 | 14.42 ± 14.69 |
| TB, mg/dl | 0.7 ± 0.3 | 0.7 ± 0.3 | 0.8 ± 0.7 |
| ALP, IU/l | 158.6 ± 182.7 | 134.9 ± 90.5 | 153.7 ± 117.0 |
| AST, IU/l | 26.4 ± 7.3 | 25.1 ± 10.5 | 28.8 ± 32.2 |
| ALT, IU/l | 31.3 ± 15.2 | 30.3 ± 18.8 | 32.2 ± 42.9 |
| WBC, /μl | 5706.0 ± 1370.6 | 6197.1 ± 2093.8 | 6240.0 ± 1864.3 |

FIG. 5

METHOD FOR PROVIDING ALERT OF POTENTIAL THYROID ABNORMALITY

TECHNICAL FIELD

The present invention relates to a system and a computer program for predicting thyrotoxicosis, and more specifically, to a system and a computer program for managing and predicting thyrotoxicosis using a wearable device.

BACKGROUND ART

Thyrotoxicosis refers to a state in which hormones secreted from a thyroid gland are excessively secreted by some cause, causing thyroid poisoning. Thereby, weight loss or fatigue may be experienced, and if severe, shortness of breath or fainting may occur. Thyrotoxicosis is considered to be a common disease having a prevalence rate of about 2%, and most patients thereof in Korea are diagnosed with Graves' disease and are treated by being administered anti-thyroid drugs. In the case of the anti-thyroid drugs, medication compliance, that is, taking drugs as prescribed, is very important in a treatment. Typically, since thyrotoxicosis has been managed only through outpatient care, there have been cases in which a patient who has been prescribed and taken drugs would often stop taking the drugs without seeking additional medical diagnosis when symptoms start to disappear after a certain period of time. In addition, even when medical care continues, an attempt to discontinue the administration of drugs is made typically after 1 to 2 years of taking the drugs at the discretion of medical staff. In any case, when a patient stops taking drugs, a relapse rate is as high as 50%, which is problematic. Even when the relapse occurs, symptoms are usually mild in the beginning. Therefore, the patient lives without feeling great discomfort until the symptoms become severe, and only then, the patients would visit a hospital finding themselves in a serious case of thyroid poisoning. In this case, the patient often needs to be hospitalized, and in some serious cases, may die eventually.

To date, thyrotoxicosis only relies on outpatient care when it comes to treating the disease and predicting the relapse thereof. When diagnosed with thyrotoxicosis, a patient should visit a clinic on a regular basis over a lifetime in principle. However, in reality, the principle is not followed, and even more so, after the patient stops taking medication. Accordingly, there is an urgent need to develop a system which enables active management of thyrotoxicosis and prediction of relapse thereof without going through outpatient care.

DISCLOSURE OF THE INVENTION

Technical Problem

An object of the present invention is to provide a system capable of managing thyrotoxicosis and predict the relapse thereof using a bio-signal of a patient, particularly a resting heart rate, measured by a wearable device.

Another object of the present invention is to provide a prediction computer program using the system.

The objects to be achieved by the inventive concept are not limited to the above-mentioned problems, and other problems that are not mentioned may be apparent to those skilled in the art from the following description.

Technical Solution

To achieve the aforementioned object, a system for predicting thyrotoxicosis using a wearable device according to an embodiment of the present invention is a system for predicting thyrotoxicosis using a resting heart rate, the system including a wearable device for measuring heart rates of a patient at regular intervals, and a bio-signal computing device for receiving heart rate information from the wearable device, the bio-signal computing device outputting a warning alarm when a resting heart rate is greater than a reference heart rate when the patient is in a normal state.

The wearable device may measure the number of steps of the patient and transmit the measured number of steps of the patient to the bio-signal computing device, and the bio-signal computing device may extract sections in which the number of steps is 0 for a predetermined period of time in a day and calculate the resting heart rate using heart rates measured in each section.

The bio-signal computing device may calculate a median value of the heart rates measured in each section and define a median value of the calculated median values as the resting heart rate.

The bio-signal computing device may calculate a median value of the heart rates measured in each section, and calculate the resting heart rate by assigning a greater weight value to a median value measured in a sleep section than to a median value measured in a wake-up section among the calculated median values.

The reference heart rate may be defined as an average value of resting heart rates measured for a predetermined number of days during which a thyroid function of the user is normal.

The bio-signal computing device may output a warning alarm when an average value of the resting heart rates for a predetermined number of consecutive days is greater than the reference heart rate.

The bio-signal computing device may calculate a median value of the heart rates measured in each section for sections in which the number of steps is 0 for at least 15 minutes in a day and define a median value of the calculated median values as the resting heart rate of the day, and may output a warning alarm when an average value of the resting heart rates for five consecutive days is greater than the reference heart rate by 10 beats per minute and more.

To achieve the other object, a computer program according to an embodiment of the present invention is embedded to a bio-signal computing device for predicting thyrotoxicosis using a resting heart rate and is stored in the medium to execute the steps of: receiving heart rates and number of steps information from a wearable device which measures the heart rates and the number of steps of a patient at regular intervals, extracting sections in which the number of steps for a predetermined period of time in a day is smaller than a predetermined value and defining the resting heart rate using heart rates measured in each section; defining an average value of resting heart rates measured for a predetermined number of days during which a thyroid function of the user is normal as a reference heart rate; and outputting a warning alarm when the resting heart rate is greater than the reference heart rate.

Specific details of other embodiments are included in the detailed description and drawings.

Advantageous Effects

As described above, according to the present invention, just by having a patient wear a wearable device, the therapeutic response, clinical progress prediction, prediction of relapse and the like with respect to thyrotoxicosis may be continuously monitored to be used for early diagnosis/treatment and the like of the relapse thereof after the discontinuation of administering medication. Also, by continuously monitoring a patient's heart rate change together with the exercise amount by using a wearable device, it is possible to increase medication compliance of the patient and to effectively predict a relapse in the case of a patient who has stopped taking medication.

To date, the management of thyrotoxicosis only relies on outpatient care, and there are no electronic devices or computer software capable of actively managing the disease and predict the relapse thereof. The inventors of the present invention have analyzed the results of clinical studies of one year and developed a prediction system and a prediction computer program of the present invention. This development is expected to be a first case to utilize digital health care in the management of thyrotoxicosis.

BRIEF DESCRIPTION OF THE DRAWINGS

FIG. 5 is a view showing thyroid hormone concentration measured at the time of a patient's visit to a clinic during a clinical study process of FIG. 4;

MODE FOR CARRYING OUT THE INVENTION

Figure 1:
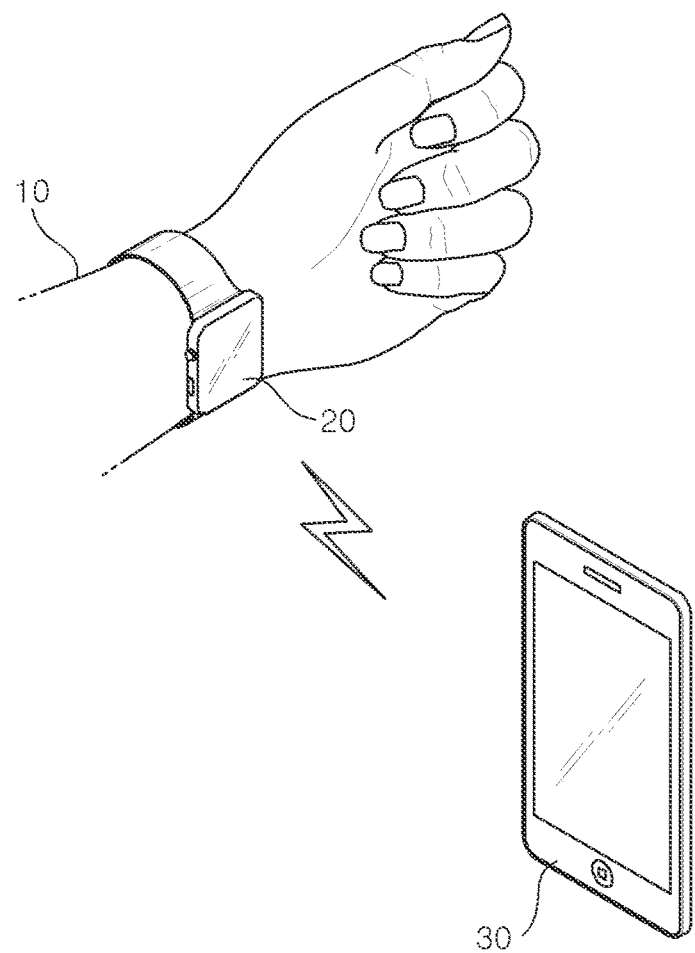
FIG. 1 is a view schematically showing a system for predicting thyrotoxicosis according to an embodiment of the present invention.

Advantages and features of the inventive concept and methods of accomplishing the same may be understood more readily by reference to the following detailed description of exemplary embodiments and the accompanying drawings. The present invention may, however, be embodied in different forms and should not be construed as limited to the embodiments set forth herein. Rather, these embodiments are provided so that this disclosure will be thorough and complete, and will fully convey the scope of the inventive concept to those skilled in the art to which the inventive concept pertains. The inventive concept will only be defined by the appended claims. The same reference numerals refer to like elements throughout the specification.

Hereinafter, a system for predicting thyrotoxicosis according to an embodiment of the present invention will be described with reference to the accompanying drawings.

Figure 2:
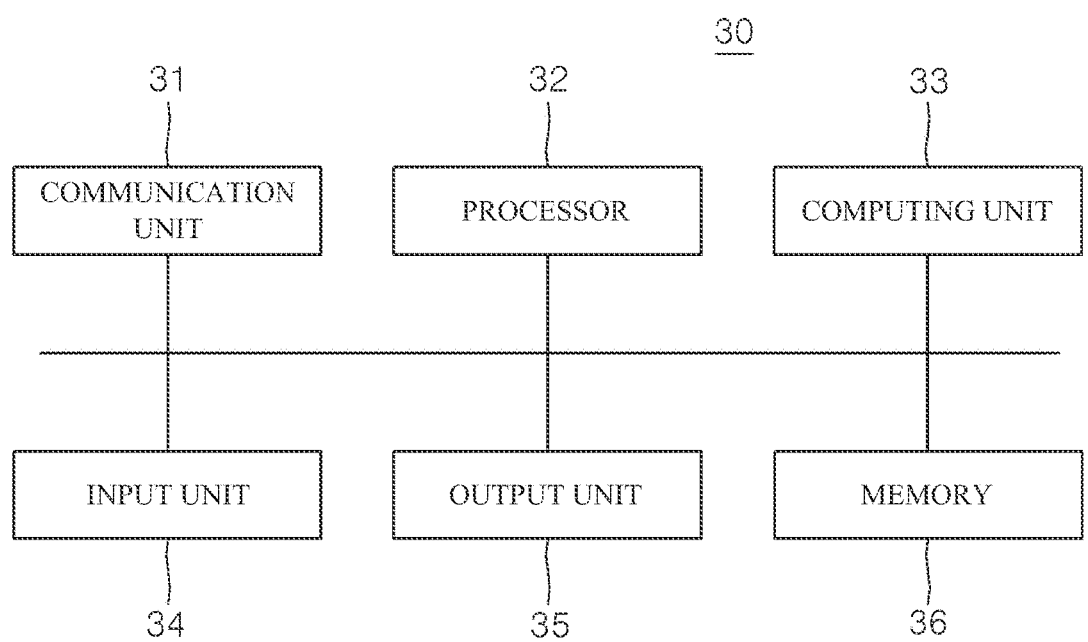
FIG. 2 is a schematic view of the configuration of a bio-signal computing device of FIG. 1.

FIG. 1 is a view schematically showing a system for predicting thyrotoxicosis according to an embodiment of the present invention. FIG. 2 is a schematic view of the configuration of a bio-signal computing device of FIG. 1. The system for predicting thyrotoxicosis of the present invention is a system for predicting thyrotoxicosis using a resting heart rate, the system including a wearable device 20 for measuring bio-signals of a patient and a bio-signal computing device 30 for communicating with the wearable device 20 to receive and compute the bio-signals.

The wearable device 20 communicates with the bio-signal computing device 30 through a network and measures bio-signals of a patient 10, for example, a heart rate and the number of steps, to transmit the bio-signals to the bio-signal computing device 30. The wearable device 20 may be linked to the bio-signal computing device 30 through wired/wireless communication, and may preferably be an electronic device capable of performing a wireless communication function such as WiFi, Bluetooth, and the like. For example, the wearable device 20 may be various devices such as a smart watch, a smart band, and the like. The wearable device 20 may include a communication module for wired/wireless communication and a sensor for measuring a heart rate and the number of steps. The sensor embedded in the wearable device 20 includes one or more sensing means for identifying the body state and the body motion of the patient 10, and may include, for example, a heart rate sensor, a gravity sensor, an acceleration sensor, a gyroscope, a GPS sensor, or a combination thereof.

It is preferable that the patient 10 always wears the wearable device 20 on his body, and the wearable device 20 may measure the heart rate of the patient 10 at regular intervals, for example, 5 to 10 times per minute. Also, the wearable device 20 measures the number of steps when the patient 10 moves.

The bio-signal computing device 30 is an electronic device which receives bio-signals from the wearable device 20 and computes the bio-signals to manage and predict thyrotoxicosis. The bio-signal computing device 30 may be an electronic device capable of performing a communication function through wireless communication while a user is moving, and may be, for example, a portable phone including a smart phone, a tablet computer, a PDA, a wearable device, a smart watch, a smart band, and the like.

The bio-signal computing device 30 includes a communication unit 31, a processor 32, a computing unit 22, an input unit 34, an output unit 35, and a memory 36.

The communication unit 31 of the bio-signal computing device 30 performs a wired/wireless communication function with an external electronic device. The communication unit 31 is responsible for data transmission/reception with the wearable device 20, and may further be responsible for data communication, voice communication, and the like with a communication company.

The computing unit 33 of the bio-signal computing device 30 uses the bio-signals received from the wearable device 20 to manage and predict thyrotoxicosis of the patient 10. Specifically, the computing unit 33 defines a reference heart rate and a resting heart rate from the measured heart rate. Here, the <heart rate> is a value measured in the wearable device 20, and the <reference heart rate> and the <resting heart rate> are values calculated from the heart rate. A process of calculating the reference heart rate and the resting heart rate is as follows.

First, the computing unit 33 extracts a section in which the number of steps is 0 for a predetermined period of time (for example, 15 minutes or more) in a day from data obtained by measuring the number of steps of a patient. The extracted section is considered to be free of the movement or the motion of the patient, and using the heart rate measured in each section, the resting heart rate is calculated. Specifically, the computing unit 33 calculates a median value (referred to as a 'median value by section') of a plurality of heart rates measured in each section and defines a median value of the median values by section calculated for one day (for example, from 0 o'clock to 24 o'clock) as the 'resting heart rate.' Since the change in heart rate may be large at the boundary of a section, an error may be greatly reduced by selecting a median value rather than an average value.

As a modified example, the computing unit 33 may calculate the resting heart rate by assigning different weight values to the median values by section calculated for one day. Specifically, sections in which the number of steps is 0 may be divided into a <wake-up section> and a <sleep section>. The <wake-up section> may be defined as a section in which the number of steps is 0 for a predetermined period of time during which a patient is awake, and the <sleep section> may be defined as a section in which the number of steps is 0 for a predetermined period of time during which the patient is in sleep. For example, a method for calculating a resting heart rate by assigning a weight value may be represented by Equation 1 below. According to Equation 1, by assigning a weight to the heart rate of the sleep section, not to the heart rate of the wake-up section, the association thereof with a thyroid function may be further increased.

Resting heart rate=[$A$×(median value of the median values by section for wake-up sections)+$B$×(median value of median values by section for sleep sections)/($A$+$B$)     [Equation 1]

(wherein, 0<$A$<$B$)

Meanwhile, the reference heart rate may be defined as an average value of resting heart rates measured for a predetermined number of days during which a patient is in a normal state (that is, when a thyroid function is normal).

As described above, the computing unit 33 defines the reference heart rate and the resting heart rate from the measured heat rates, and then, when the resting heart rate is greater than the reference heart rate, outputs a warning alarm through the output unit 35 or the wearable device 20. Preferably, the computing unit 33 may output a warning alarm when an average value of resting heart rates of a predetermined number of consecutive days (for example, 5 consecutive days or more) is greater than the reference heart rate by a predetermined value (for example, 10 beats per minute) or more. In the present invention, the difference between the resting heart rate and the reference heart rate is used to manage and predict thyrotoxicosis. The correlation among the resting heart rate, the reference heart rate and thyrotoxicosis will be described in detail later.

The input unit 34 of the bio-signal computing device 30 includes a software or hardware input device, and the output unit 35 includes a speaker and a display. The display may include a user interface as a means for sensing the user's touch input in a UI/UX of an operating system software and a UI/UX of an application software. The display may be composed of a touch screen which is a means for outputting a screen and which executes a function of an input means for sensing the user's touch event.

The memory 36 of the bio-signal computing device 30 generally provides a space to store computer codes and data used in a device. The memory 36 may store not only various applications and resources required for the driving/management thereof, but also firmware for any device including a basic input/output system, an operating system, various programs, applications, or user interface functions executed on a device, processor functions, and the like.

The processor 32 of the bio-signal computing device 30 executes the computer codes with the operating system and executes an operation of generating and using data. In addition, the processor 32 may receive and process input and output data between components of the bio-signal computing device 30 using a series of commands. Also, the processor 32 serves as a control unit for executing functions of the operating system software and various application software installed in the bio-signal computing device 30.

Although additional or common components of a hardware/software module and the like such as a power supply unit, a communication modem, a GPS, an I/O device, and a camera module are not shown in the drawings, the bio-signal computing device 30 of the present invention may include a variety of internal and external components which contribute to the function of the device. The bio-signal computing device 30 may also include hardware elements (including circuits), software elements (including computer code stored in a computer-readable medium), or a combination of the hardware elements and the software elements.

In the present embodiment, the wearable device 20 and the bio-signal computing device 30 are exemplarily described to be physically separated, but the present invention is not limited thereto. That is, the bio-signal computing device 30 may be physically integrated in the wearable device 20, in which case the wearable device 20 and the bio-signal computing device 30 should be considered to be an integrated single physical electronic device.

Figure 3:
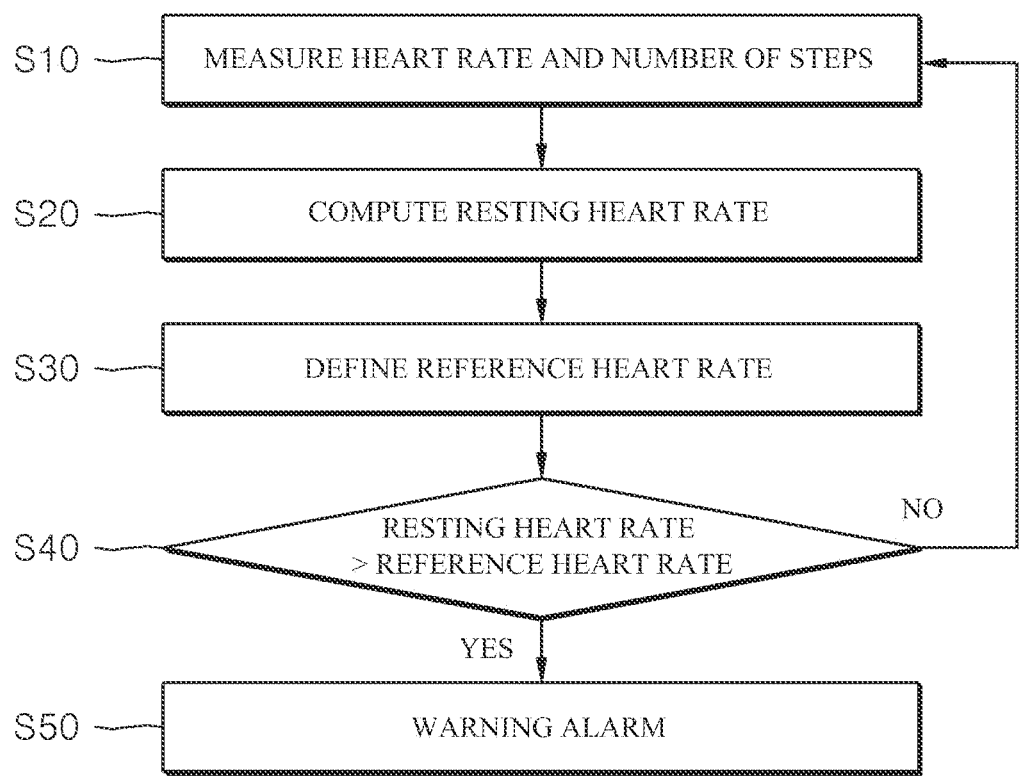
FIG. 3 is a flow chart sequentially showing a method for predicting thyrotoxicosis according to an embodiment of the present invention.

Hereinafter, referring to FIG. 3, a method for predicting thyrotoxicosis according to an embodiment of the present invention will be described in detail. FIG. 3 is a flow chart sequentially showing a method for predicting thyrotoxicosis according to an embodiment of the present invention.

First, the wearable device 20 measures the number of steps of the patient 10 and the heart rate at regular intervals and send the same to the bio-signal computing device 30 S10.

The bio-signal computing device 30 receives heart rates and the numbers of steps from the wearable device 20 and computes a resting heart rate S20. Specifically, the bio-signal computing device 30 extracts sections in which the number of steps is 0 for a predetermined period of time (for example, 15 minutes or more) in a day from data of the number of steps of the patient. The bio-signal computing device 30 calculates a median value by section for heart rates of each section and defines a median value of the median values by section as the resting heart rate based on a day. As a modified example, the bio-signal computing device 30 may calculate a resting heart rate by assigning a greater weight value to the heart rate of a sleep section than to the heart rate of a wake-up section as shown in Equation 1.

Also, the bio-signal computing device 30 defines an average value of resting heart rates measured for a predetermined number of days during which a patient's thyroid function is in a normal state as a 'reference heart rate.' S30

Thereafter, the bio-signal computing device 30 compares values of the resting heart rate and the reference heart rate S40 and outputs a warning alarm S50 through its own output unit or the wearable device 20 when the resting heart rate is greater than the reference heart rate. For example, the bio-signal computing device 30 may output a warning alarm when an average value of resting heart rates of a predetermined number of consecutive days (for example, 5 consecutive days or more) is greater than the reference heart rate by a predetermined value (for example, 10 beats per minute) or more.

Hereinafter, referring to FIG. 4 to FIG. 8, details of clinical studies on the correlation between heart rates and thyrotoxicosis on which the prediction system of the present invention is based will be described in detail.

Figure 4:
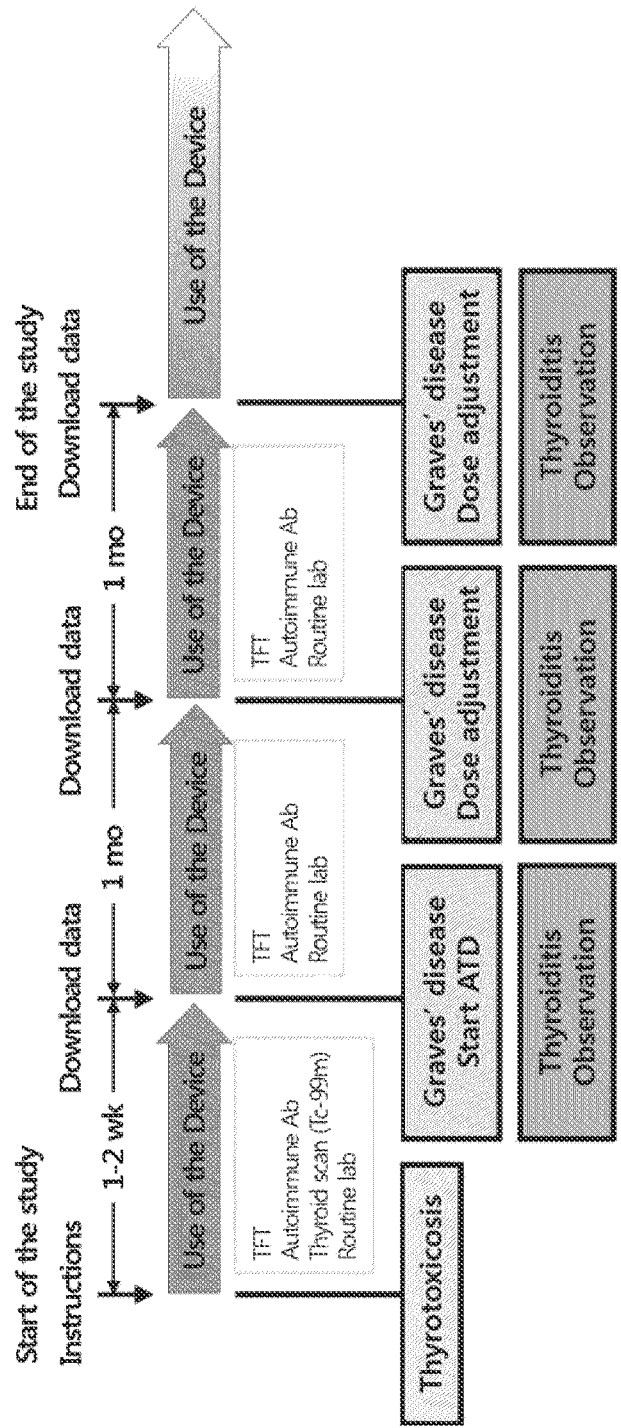
FIG. 4 is a view schematically showing a clinical method using the prediction system of the present invention.

FIG. 4 is a view schematically showing a clinical method using the prediction system of the present invention. In the clinical studies, in order to confirm the association between a thyroid function and heart rates, 30 thyrotoxicosis patients (including new patients and relapse patients) were recruited and asked to wear a wearable device and their heart rates were continuously monitored. The wearable devices used in the present clinical studies was Fitbit Charge HR™ and Fitbit Charge 2™. The patients wearing the wearable device visited a clinic three times and subjected to anti-thyroid drug treatment, and the change in thyroid hormone concentration during the treatment was compared with the change in heart rate measured using the wearable device. In addition, in order to compare the degree of association between the change in heart rate measured by the wearable device and the change in thyroid function with that of a typical method, heart rates measured by an automatic blood pressure monitor at the time of the visit to the clinic and hyperthyroidism symptom scales (HSS) were both measured and analyzed each time of the visit to the clinic.

FIG. 5 is a view showing thyroid hormone concentration measured at the time of a patient's visit to a clinic during a clinical study process of FIG. 4. In FIG. 5, BMI stands for Body Mass Index, SBP stands for Systolic Blood Pressure, DBP stands for Diastolic Blood Pressure, HR stands for Heart Rate, HSS stands for Hyperthyroid Symptom Scale), free T4 stands for thyroid hormone, TSH stands for Thyroid Stimulating Hormone, TB stands for Total Bilirubin, ALP stands for Alkaline Phosphorous, AST stands for Aspartate Transaminase, ALT stands for Alamine Transaminase, and WBC stands for White Blood Cells. As the anti-thyroid treatment continued to be performed on patients with thyrotoxicosis, the numerical values of thyroid hormone (free T4), which is measured at the time of the second and third visits to the clinic was gradually decreased to be within a normal range (0.8-1.8 ng/dL) when compared with the numerical value thereof measured at the first visit to the clinic.

Figure 6:
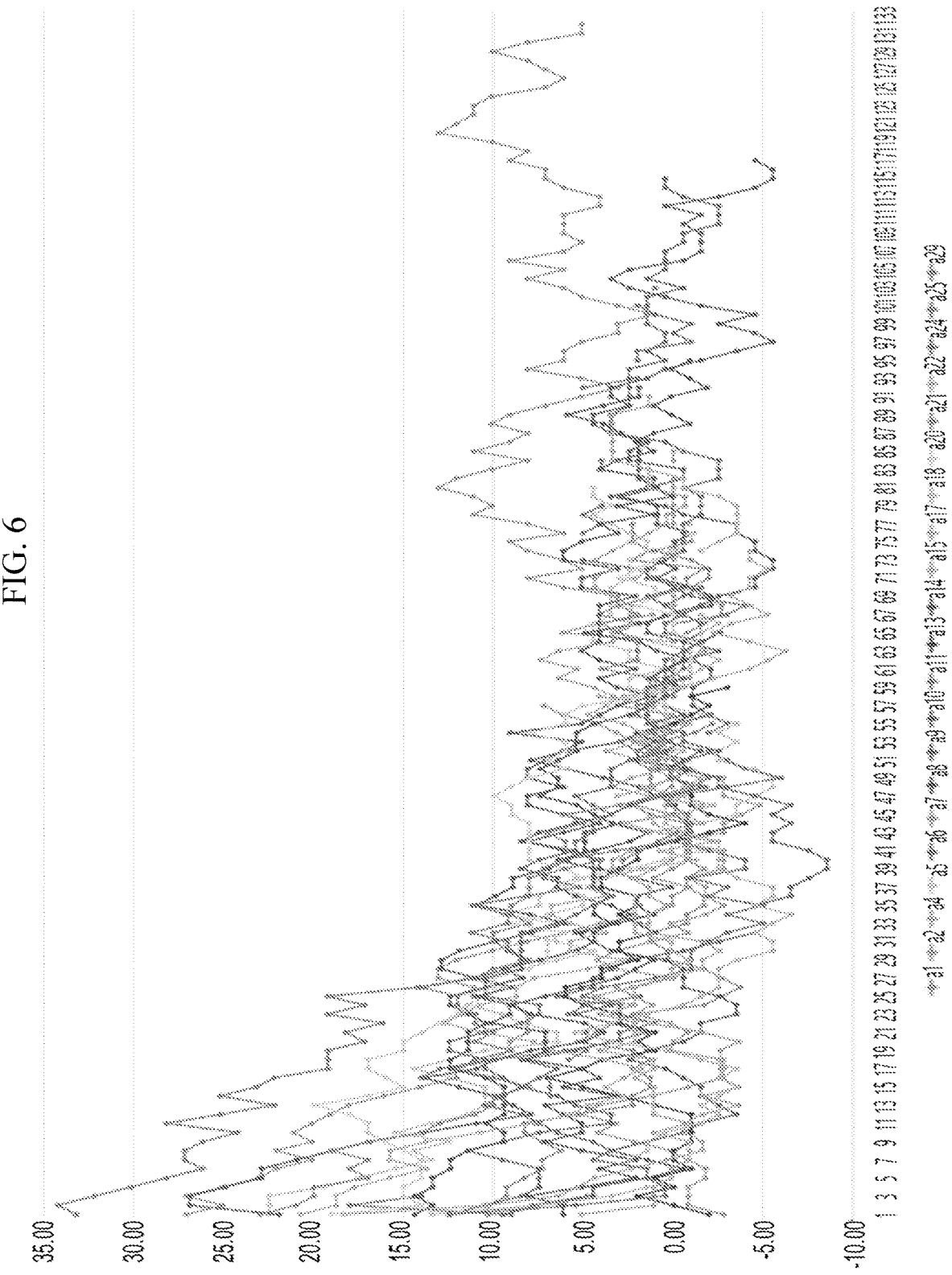
FIG. 6 is a view showing a resting heart rate measured during the clinical study of FIG. 4.

FIG. 6 is a view showing a resting heart rate measured during the clinical study of FIG. 4. Specifically, FIG. 6 shows a change in resting heart rate over time measured by a wearable device. It was confirmed that as the anti-thyroid treatment continued to be performed on the patients with thyrotoxicosis, the resting heart rate measured with the wearable device gradually decreased.

Figure 7:
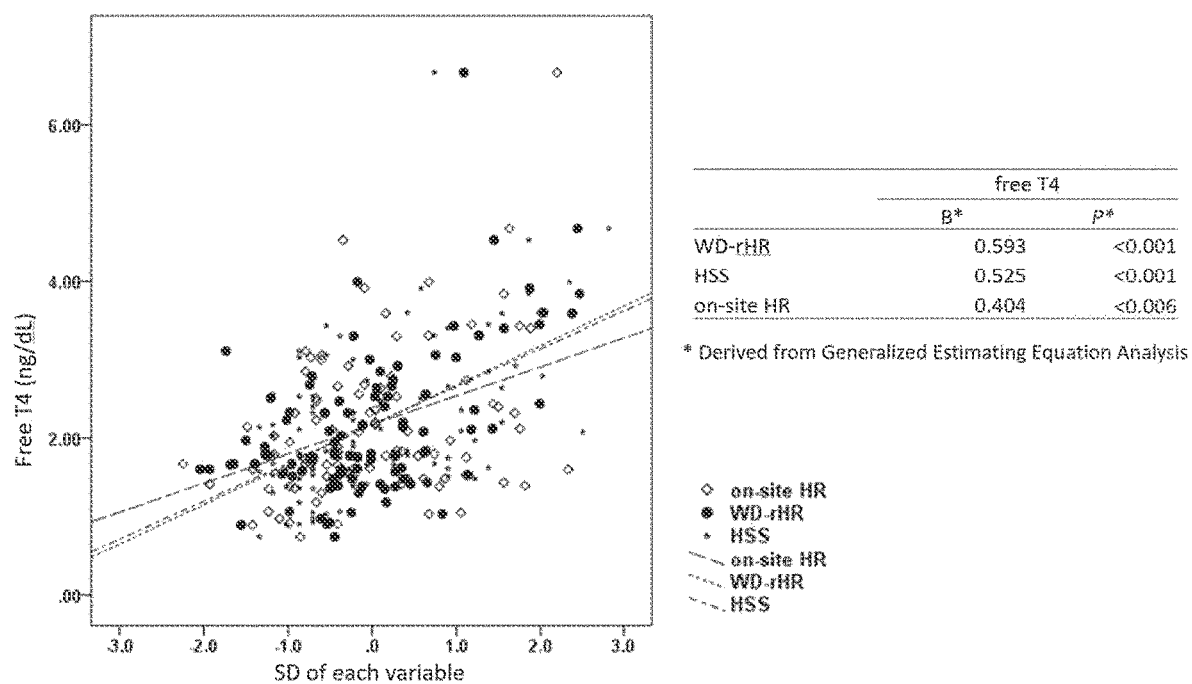
FIG. 7 is a graph showing the association between thyroid hormone concentration and the resting heart rate measured during the clinical study of FIG. 4.

As described above, the correlation between the measured heart rate and the thyroid hormone concentration was examined. FIG. 7 is a graph showing the association between thyroid hormone concentration and the resting heart rate measured during the clinical study of FIG. 4. In FIG. 7, WD-rHR is a resting heart rate obtained through a wearable device, HSS represents a value obtained by adding scores of items represented by 0-5 points on 10 representative symptoms of thyrotoxicosis on a survey, and on-site HR (or HR) is a heart rate measured with a blood pressure monitor at a clinic at the time of the visit to the clinic on a day when a blood test was conducted. In order to compare the heart rate data (WD-rHR and on-site HR) and the HSS data, standard deviations for the average of each index were used. In this case, the resting heart rate (WD-rHR) measured with the wearable device turned out to be the most relevant.

Figure 8:
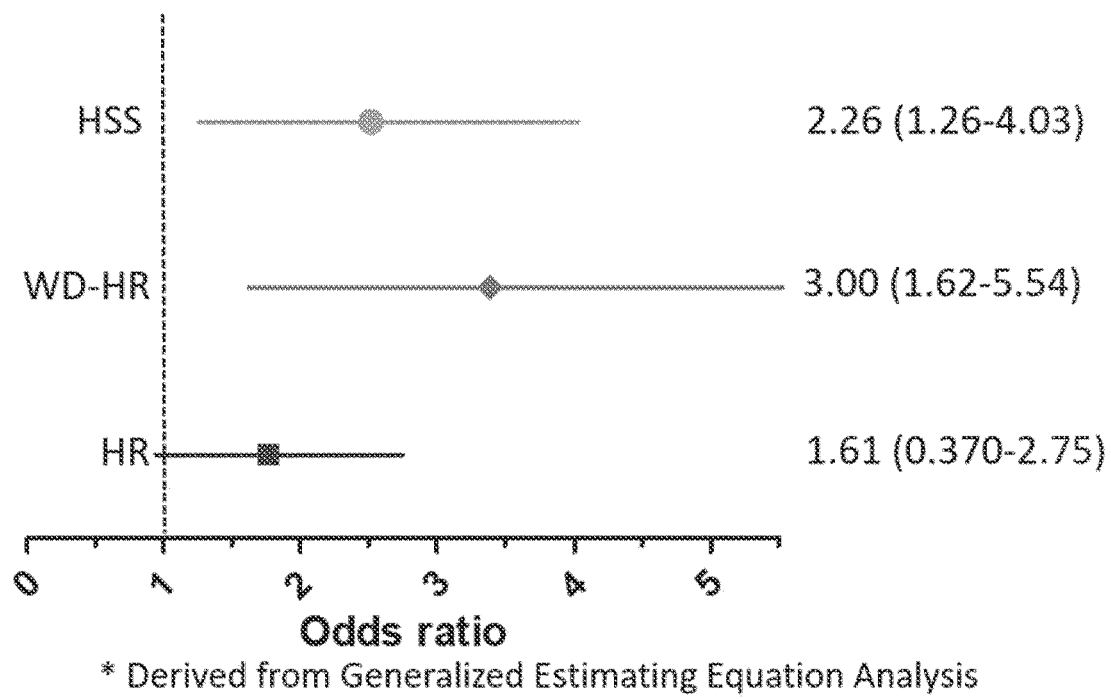
FIG. 8 is a graph showing the association between the change in the resting heart rate measured with a wearable device during the clinical study of FIG. 4 and thyrotoxicosis.

FIG. 8 is a graph showing the association between the change in the resting heart rate measured with a wearable device during the clinical study of FIG. 4 and thyrotoxicosis. Specifically, FIG. 8 shows the probability of being classified as thyrotoxicosis when each index increases by 1 standard deviation (SD) by dividing the data of FIG. 7 into cases in which the thyroid hormone (free T4) is greater than 1.8 ng/dL (that is, greater than an upper limit of a normal state, thereby being within a range of thyrotoxicosis) and not. In the case of a resting heart rate (WD-HR) measured with a wearable device, it has been found that when the resting heart rate increases by 1SD (about 10 beats per minute), the possibility of being classified as thyrotoxicosis increases three times. The above results show that a single index which is the resting heart rate (WD-HR) measured with a wearable device is more excellent in predictability than the index (HSS) in which various symptoms of thyrotoxicosis are scored. The heart rate (HR) typically measured at the time of the visit to a clinic did not show a statistically meaningful predictability of thyrotoxicosis.

As described above, it has been confirmed the change in resting heart rate measured by the wearable device has a close relationship with the prevalence or recurrence of thyrotoxicosis. When the prediction system of the present invention is used, just by having a patient wear a wearable device without having to visit a doctor's clinic, the degree of control of thyrotoxicosis may be evaluated and the relapse thereof may be easily predicted from the change in resting heart rate. When a resting heart rate increases abnormally compared with a reference heart rate, the prediction system may alert the patient to receive a blood test by warning the patient of thyroid function abnormalities.

Although the inventive concept has been described with reference to the accompanying drawings, it will be understood by those having ordinary skill in the art to which the present invention pertains that various changes in form and details may be made therein without departing from the spirit and scope of the inventive concept. It is therefore to be understood that the above-described embodiments are illustrative in all aspects and not restrictive.

The invention claimed is:

1. A method of managing a thyroid abnormality of a person, the method comprising:

acquiring, using a wearable device worn by the person, a plurality of heart rates during at least a first consecutive days and a second consecutive days, wherein the first consecutive days comprise a first day in which a thyroid function of the person is assessed as normal through a blood test, wherein the person is treated for improving the thyroid function, as a result, the thyroid function of the person is normal on the first day, wherein the second consecutive days comprise a second day in which the thyroid function of the person is unknown, wherein the second day is later than the first day, and wherein the number of the first consecutive days is same as the number of the second consecutive days and is greater than 1;

computing, on a bio-signal computing device, a reference resting heart rate using heart rates that meet a predetermined standard among the heart rates of the first consecutive days, wherein the predetermined standard is set for selecting heart rates on a period free of motion or movement, and wherein the predetermined standard is related to a sensing value of a gravity sensor, an acceleration sensor, a gyroscope, a GPS sensor, or a combination thereof;

computing, on a bio-signal computing device, a current resting heart rate using heart rates that meet the predetermined standard among the heart rates of the second consecutive days;

determining, on the bio-signal computing device, a prediction result related to a thyroid function state of the second day using the current resting heart rate and the reference resting heart rate of the person; and inducing to conduct an additional blood test on the person based on the prediction result.

2. The method of claim 1,
wherein computing the reference resting heart rate comprises:
identifying time segments regarded as having no movement or motion and selecting heart rates for each of the identified time segments among heart rates of the first consecutive days, and
calculating the reference resting heart rate using the selected heart rates among heart rates of the first consecutive days, and
wherein computing the current resting heart rate comprises:
identifying time segments regarded as having no movement or motion and selecting heart rates for each of the identified time segments among heart rates of the second consecutive days, and
calculating the reference resting heart rate using the selected heart rates among heart rates of the second consecutive days.

3. The method of claim 2,
wherein the reference resting heart rate is a median or average value of the selected heart rates among heart rates of the first consecutive days, and
wherein the current resting heart rate is a median or average value of the selected heart rates among heart rates of the second consecutive days.

4. The method of claim 1,
wherein the treating for improving the thyroid function comprises an anti-thyroid drug treatment for decreasing free T4 in the person.

5. The method of claim 1,
wherein the wearable device and the bio-signal computing device are physically separate devices.

6. The method of claim 1,
wherein the wearable device and the bio-signal computing device are an integrated single physical electronic device.

7. The method of claim 1,
wherein determining comprises determining whether the current resting heart rate is greater than the reference resting heart rate by a predetermined value or more.

8. The method of claim 1,
wherein the blood test is detecting a hormone level at least free T4 or TSH.

9. The method of claim 1, further comprising conducting the additional blood test on the person based on the prediction result.

* * * * *